US00PP20198P2

(12) United States Plant Patent
Blom

(10) Patent No.: US PP20,198 P2
(45) Date of Patent: Aug. 4, 2009

(54) *VERONICA* PLANT NAMED 'BABY BLUE'

(50) Latin Name: ***Veronica austriaca*×*Veronica spicata***
Varietal Denomination: Baby Blue

(75) Inventor: Walter Blom, Hillegom (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/214,239

(22) Filed: Jun. 16, 2008

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent L Bell
(74) *Attorney, Agent, or Firm*—C. A. Whealy

(57) ABSTRACT

A new and distinct cultivar of *Veronica* plant named 'Baby Blue', characterized by its upright plant habit, freely flowering habit; dark blue-colored flowers; and good garden performance.

2 Drawing Sheets

Botanical designation: *Veronica austriaca*×*Veronica spicata.*
Cultivar denomination: 'Baby Blue'.

BACKGROUND OF THE INVENTION

The present invention relates to a new and distinct cultivar of *Veronica,* botanically known as *Veronica austriaca*× *Veronica spicata* and hereinafter referred to by the name 'Baby Blue'.

The new *Veronica* is a product of a planned breeding program conducted by the Inventor in Hillegom, The Netherlands. The objective of the breeding program is to create new *Veronica* cultivars with numerous attractive flowers and good garden performance.

The new *Veronica* originated from a cross-pollination of an unnamed proprietary selection of *Veronica austriaca,* not patented, as the female, or seed, parent with an unnamed proprietary selection of *Veronica spicata,* not patented, as the male, or pollen, parent. The new *Veronica* was discovered and selected by the Inventor as a single flowering plant from within the progeny of the stated cross-pollination grown in a controlled greenhouse environment in Hillegom, The Netherlands in June, 2004.

Asexual reproduction of the new cultivar by vegetative cuttings in a controlled greenhouse environment in Hillegom, The Netherlands, since 2006, has shown that the unique features of this new *Veronica* are stable and reproduced true to type in successive generations.

SUMMARY OF THE INVENTION

Plants of the new *Veronica* have not been observed under all possible environmental conditions. The phenotype may vary somewhat with variations in environment such as temperature and light intensity without, however, any variance in genotype.

The following traits have been repeatedly observed and are determined to be the unique characteristics of 'Baby Blue'. These characteristics in combination distinguish 'Baby Blue' as a new and distinct cultivar:

1. Upright plant habit.
2. Freely flowering habit.

3. Dark blue-colored flowers.
4. Good garden performance.

Plants of the new *Veronica* differ from plants of the parent selections primarily in plant height and flower color.

Plants of the new *Veronica* can be compared to plants of *Veronica* 'Ulster Dwarf Blue', not patented. In side-by-side comparisons conducted by the Inventor in Hillegom, The Netherlands, plants of the new *Veronica* differed from plants of 'Ulster Dwarf Blue' in the following characteristics:

1. Plants of the new *Veronica* were slightly taller than plants of 'Ulster Dwarf Blue'.
2. Plants of the new *Veronica* were more freely flowering than plants of 'Ulster Dwarf Blue'.
3. Plants of the new *Veronica* had better postproduction longevity than plants of 'Ulster Dwarf Blue'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph on the first sheet comprises a side perspective view of a typical flowering plant of 'Baby Blue' grown in a container.

The photograph at the top of the second sheet is a close-up view of typical inflorescences of 'Baby Blue'.

The photograph at the bottom of the second sheet is a close-up view of typical leaves of 'Baby Blue'.

DETAILED BOTANICAL DESCRIPTION

Plants used for the aforementioned photographs and following description were grown under conditions which closely approximate commercial production conditions during the summer in an outdoor nursery in Hillegom, The Netherlands for two years. During the production of the plants, day temperatures ranged from 13° C. to 27° C. and night temperatures ranged from 4° C. to averaged 15° C. In the following description, color references are made to The Royal Horticultural Society Colour Chart, 2001 Edition, except where general terms of ordinary dictionary significance are used.

Botanical classification: *Veronica austriaca*×*Veronica spicata* cultivar Baby Blue.

Parentage:

*Female, or seed, parent.*—Unnamed proprietary selection of *Veronica austriaca,* not patented.

*Male, or pollen, parent.*—Unnamed proprietary selection of *Veronica spicata,* not patented.

Propagation:

*Type cutting.*—Vegetative cuttings.

*Time to initiate roots.*—About three weeks at 20° C.

*Root description.*—Fine, fibrous; white in color.

Plant description:

*Type/form.*—Herbaceous perennial. Upright, broadly columnar plant form. Freely basal branching with about 15 main stems.

*Plant height.*—About 23.2 cm.

*Plant width.*—About 20 cm.

*Lateral branch description.*—Length: About 5.5 cm. Diameter: About 1.7 mm. Internode length: About 2.7 cm. Strength: Strong. Texture: Densely pubescent. Color: Close to 137B.

Foliage description:

*Arrangement.*—Opposite, simple.

*Length.*—About 4.5 cm.

*Width.*—About 1.8 cm.

*Shape.*—Ovate.

*Apex.*—Broadly acute.

*Base.*—Attenuate.

*Margin.*—Serrate.

*Texture, upper and lower surfaces.*—Sparsely pubescent.

*Venation pattern.*—Pinnate.

*Color.*—Developing foliage, upper surface: Between 138A and 143A. Developing foliage, lower surface: Close to 147A to 147B. Fully expanded foliage, upper surface: Close to 137A; venation, close to 144B. Fully expanded foliage, lower surface: Between 137B and 147B; venation, close to 144B to 144C.

*Petiole length.*—About 2.3 cm.

*Petiole diameter.*—About 3 mm by 1.5 mm.

*Petiole texture, upper and lower surfaces.*—Sparsely pubescent.

*Petiole color, upper and lower surfaces.*—Close to 144B; on the upper surface towards the base, close to 145A.

Flower description:

*Flower arrangement and shape.*—Single campanulate flowers arranged on terminal racemes; flowers face mostly outwardly; flowers sessile. Freely flowering, about 140 flowers per inflorescence.

*Fragrance.*—Faint; sweet and pleasant.

*Natural flowering season.*—Flowering continuous from mid to late summer in The Netherlands.

*Flower longevity on the plant.*—About one week; flowers not persistent.

*Flower buds.*—Length: About 5 mm. Diameter: About 2 mm. Shape: Oblong. Color: Close to 93B to 93C.

*Inflorescence height.*—About 12.6 cm.

*Inflorescence diameter.*—About 2.2 cm.

*Flower diameter.*—About 7 mm.

*Flower height* (*depth*).—About 1.1 cm.

*Petals.*—Arrangement: Four, fused about 37.5% from the base. Length: about 1 cm. Width: About 2 mm to 3 mm. Shape: Oblanceolate. Apex: Broadly acute. Margin: Entire. Texture, upper and lower surfaces: Smooth, glabrous. Color: When opening and fully opened, upper surface: Close to 93B; towards the base, close to 92D. Color becoming closer to N93A. When opening and fully opened, lower surface: Close to 93B; towards the base, close to 92D.

*Calyx.*—Shape: Four sepals fused in a tube; ovate; apices, acute. Length: About 4 mm. Width: About 3 mm. Texture, upper and lower surfaces: Smooth, glabrous. Color, immature, upper and lower surfaces: Close to 138B. Color, mature, upper surface: Close to 137C. Color, mature, lower surface: Close to 137B to 137C.

*Peduncles.*—Strength: Strong. Length: About 12.3 cm. Diameter: About 2 mm. Aspect: Mostly upright. Texture: Smooth, glabrous. Color: Close to 138B.

*Reproductive organs.*—Stamens: Quantity per flower: Two. Filament length: About 7 mm. Filament color: Close to 93C to 93D. Anther shape: Elliptic. Anther length: About 2 mm. Anther color: Close to N92C to N92D; color becoming closer to 11D with development. Pollen amount: Scarce. Pollen color: Close to 11A. Pistils: Quantity per flower: One. Pistil length: About 1.2 cm. Stigma shape: Clavate. Stigma color: Close to N92B. Style length: About 1.1 cm. Style color: Close to 93B. Ovary color: Close to 143B.

*Fruits.*—Length: About 3 mm. Diameter: About 2 mm. Color: Close to 138A.

*Seeds.*—Quantity per fruit: About ten. Length: About 1 mm. Diameter: About 0.7 mm. Color: Close to 200C to 200D.

Disease/pest resistance: Plants of the new *Veronica* have not been noted to be resistant to pathogens and pests common to *Veronica.*

Garden performance: Plants of the new *Veronica* have exhibited good tolerance to rain and wind and have been observed to tolerate temperatures ranging from −30° C. to 30° C.

It is claimed:

1. A new and distinct *Veronica* plant named 'Baby Blue' as illustrated and described.

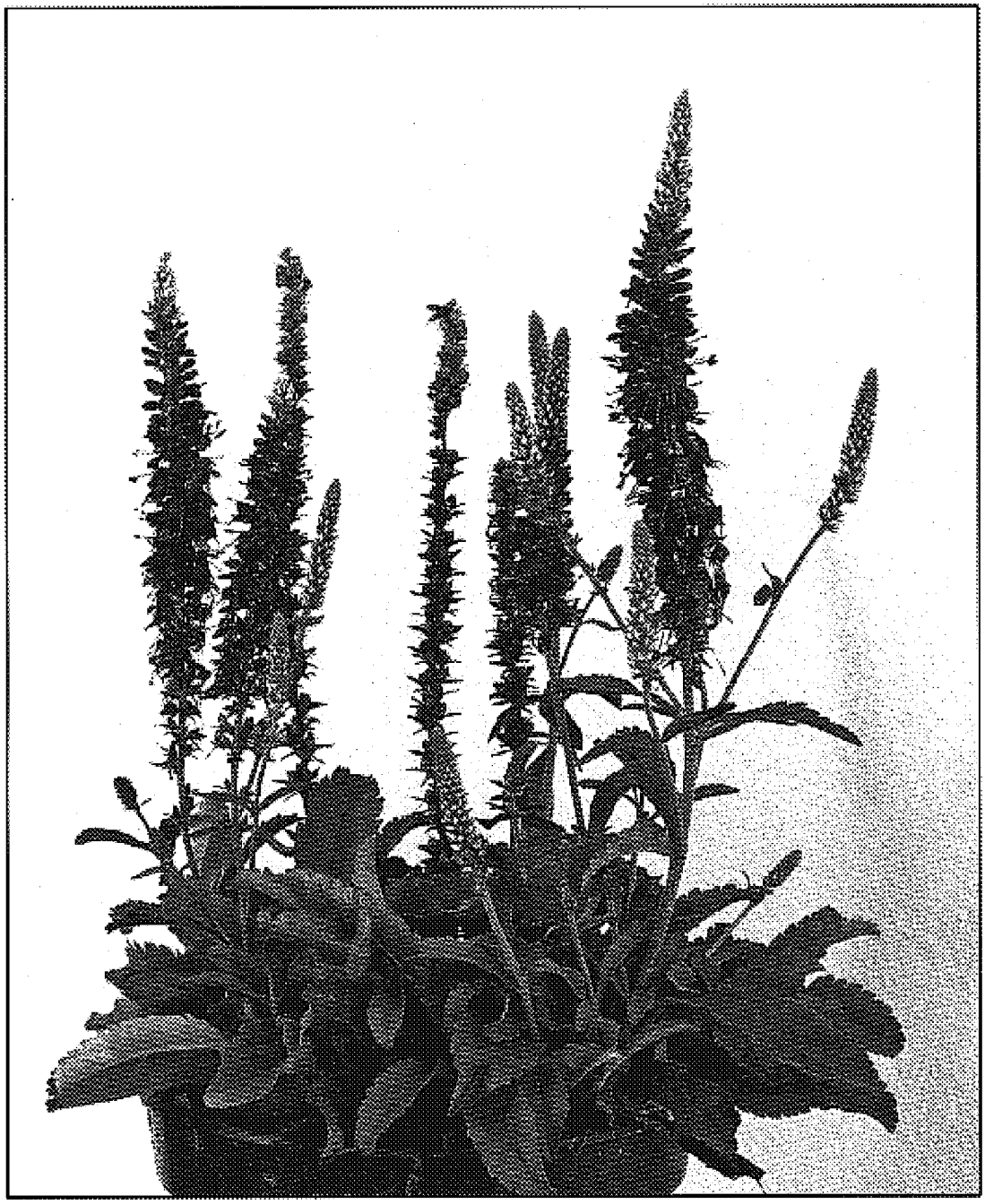

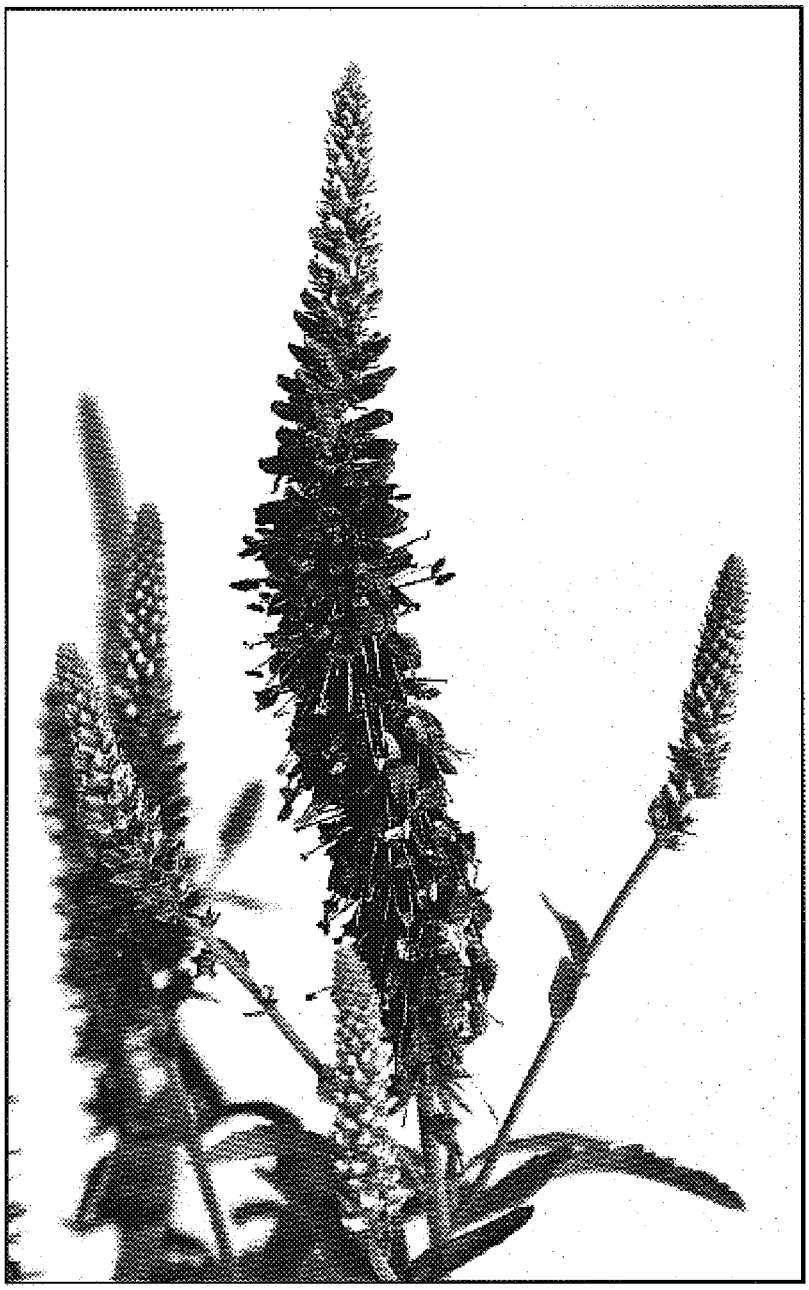
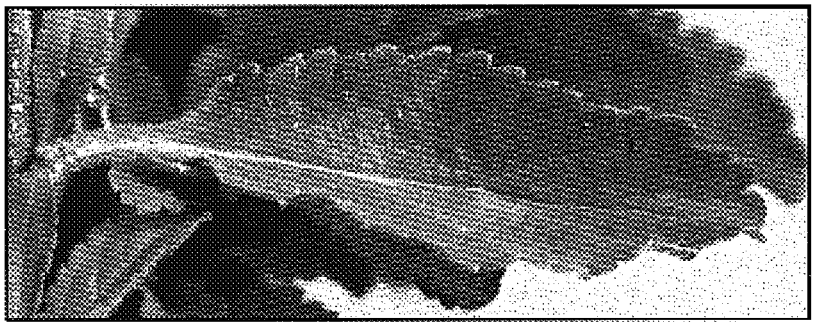

* * * * *